United States Patent [19]

Hall et al.

[11] Patent Number: 4,689,328

[45] Date of Patent: Aug. 25, 1987

[54] PROCESS FOR CONTROLLING HYPERLIPIDEMIA

[75] Inventors: Iris H. Hall; George H. Cocolas, both of Chapel Hill, N.C.

[73] Assignee: Research Corporation, New York, N.Y.

[21] Appl. No.: 815,337

[22] Filed: Dec. 31, 1985

[51] Int. Cl.$^4$ .......................................... A61K 31/505
[52] U.S. Cl. .................................... 514/274; 514/275
[58] Field of Search ................ 514/269, 272, 274, 275

[56] References Cited

PUBLICATIONS

Journal of Pharmaceutical Sciences, vol. 73, No. 12, Dec. 1984; Hall et al.
J. Med. Chem., vol. 10, 248 and 290 (1967), Borodkin et al.
J. Med. Chem., vol. 10, 290 (1967), Borodkin et al.
J. Amer. Chem. Soc., vol. 43, 19 (1910), Wheeler et al.

Primary Examiner—Leonard Schenkman
Assistant Examiner—Joseph A. Lipovsky
Attorney, Agent, or Firm—Scully, Scott, Murphy & Presser; 42

[57] ABSTRACT

A process for controlling hyperlipidemia in mammals is disclosed. In this process a mammal suffering from hyperlipidemia is treated with a hyperlipidemia controlling effective amount of a compound having the structural formula

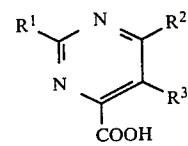

wherein $R^1$ is mercapto, amino, hydroxy or $C_1$–$C_4$ alkylthio; $R^2$ is amino, hydroxy or mercapto; and $R^3$ is hydrogen, $C_1$–$C_6$ alkyl, $C_7$–$C_9$ alkoxyphenyl or $C_7$–$C_9$ aralkyl.

In another aspect of the present invention a pharmaceutical composition comprising the above compound in combination with a pharmaceutically acceptable carrier therefor is provided.

11 Claims, No Drawings

PROCESS FOR CONTROLLING HYPERLIPIDEMIA

BACKROUND OF THE DISCLOSURE

1. Field of the Invention

The present invention is directed to a process for controlling hyperlipidemia. More specifically, the present invention is directed to a process for controlling hyperlipidemia by treating that condition with a class of 4-pyrimidinecarboxylic acids.

2. Background of the Prior Art

Hyperlipidemia, a condition associated with elevated serum cholesterol, phospholipid and/or triglycerides blood levels, is the base cause of a whole class of illnesses which exact a terrible toll in death and infirmity, as well as economic loss associated with lost productive activity and expensive medical treatment. It is only necessary to mention one of the most serious conditions known in man, arthereosclerosis, probably the most serious of the hyperlipidemic induced illnesses, to appreciate the importance of developing treatment regimes effective in controlling this condition.

Because of the importance of hyperlipidemia, many compounds have been proposed to lower serum cholesterol, phospholipid and triglycerides blood levels in mammals. For example, U.S. Pat. No. 4,499,303 discloses a novel class of N-benzoyl and N-benzoylsulfamates as well as benzoylsulfonamides useful in this application.

Another class of compounds disclosed as useful in reducing serum cholesterol and triglycerides blood levels in mammals is U.S. Pat. No. 4,395,417. This patent describes the use of cyclic imides, diones, reduced diones and analogs thereof useful in this application.

Windmueller and his co-workers have demonstrated that 1 percent orotic acid (2,6-dihydroxy-4-pyrimidinecarboxylic acid) decreases the plasma lipids blood level in rats when the rats are fed a diet of this compound. Windmueller *Biochem. Biophys. Res. Commun.*, Vol. 11, 496 (1963); Windmueller, *J. Biol. Chem.*, Vol. 239, 330 (1964); Windmueller and Spaeth, *J. Biol. Chem.*, Vol. 241, 2891 (1966); and Windmueller and Levy, *J. Biol. Chem.*, Vol. 242, 2246 (1967). Ravi Subbiah, *J. Steroid Biochem.*, Vol. 9, 775 (1978) later showed that both serum cholesterol and triglycerides blood levels were also reduced when rats were treated with 1 percent orotic acid. However, this study indicated that cholesterol, fatty acid and triglyceride blood levels in the liver of the treated rats were increased along with a corresponding decrease in cholesterol excretion into the bile and feces. That is, this treatment can lead to fatty liver disease.

Subsequent studies demonstrated that orotic acid reduced serum lipoprotein fractions, i.e., low-density lipoprotein, very low-density lipoprotein and high-density lipoprotein induced hyperlipidemia states in animals. P. S. Roheim et al., *Biochem. Biophys. Res. Commun.*, Vol. 20, 416 (1965); R. Fears et al., *Biochem. Soc. Trans.*, Vol. 6, 602 (1978); and L. A. Pottengen et al., *J. Lipid Res.*, Vol. 12, 450 (1971). It is noted that the Roheim et al. study indicated that protein synthesis, required for the apoprotein, was not inhibited. Rather, there was an inability to incorporate the lipid with the apoprotein for the lipoprotein fractions by the liver.

Compounds that are arguably structurally similar to orotic acids, all characterized as 4-pyrimidinecarboxylic acids, are known in the art. S. Borodkin et al., *J. Med. Chem.*, Vol. 10, 248(1967) and *J. Med. Chem.*, Vol. 10, 290 (1967) and H. L. Wheeler et al., *J.A.C.S.*, Vol. 43, 19 (1910). These papers, although directed to 4-pyrimidecarboxylic acids, do not disclose or suggest the use of these compounds as hypolipidemic agents.

Although the above discussion emphasizes the use of orotic acid as a hypolipidemic agent, the concentration required to produce this effect is deemed too high. Those skilled in the art are aware of the criticality of employing low doses of therapeutic compounds in order to preclude undesirable side effects. As a general rule, high concentrations of any therapeutic compounds are dangerous. Thus, there is an established need in the art to provide compounds having the useful effects, provided by orotic acid, but which are effective at lower concentrations.

In addition to a perceived need in the art for providing hypolipidemic agents which are effective in mammals at low concentrations, it is also important to develop hypolipidemic agents that do not lead to fatty liver disease.

DESCRIPTION

A class of compounds have now been discovered which exhibit significant hypolipidemic activity in mammals at low concentration and which do not increase cholesterol, fatty acid or triglycerides level in the liver of mammals which are treated therewith.

In accordance with the present invention a process for controlling hyperlipidemia is provided. In this process mammals subject to hyperlipidemia are treated with a hyperlipidemia controlling effective amount of a compound having the structural formula

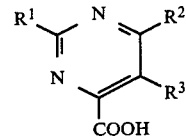

where $R^1$ is mercapto, amino, hydroxy or $C_1$–$C_4$ alkylthio; $R^2$ is amino, hydroxy or mercapto; and $R^3$ is hydrogen, $C_1$–$C_6$ alkyl, $C_7$–$C_8$ alkoxyphenyl or $C_7$–$C_9$ aralkyl.

In further accordance with the present invention a composition is provided. This therapeutic composition comprises a hyperlipidemia controlling effective amount of a compound having the structural formula

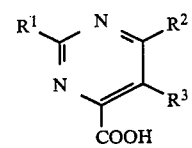

where $R^1$ is mercapto, amino, hydroxy or $C_1$–$C_4$ alkylthio; $R^2$ is amino, hydroxy or mercapto; and $R^3$ is hydrogen, $C_1$–$C_6$ alkyl, $C_7$–$C_9$ alkoxyphenyl or $C_7$–$C_9$ aralkyl and a pharmaceutically acceptable carrier therefor.

DETAILED DESCRIPTION

The present invention is directed to a process for controlling hyperlipidemia in mammals. Thus, the instant invention is directed to a process for controlling a whole host of mammalian diseases associated with increased serum cholesterol, serum triglycerides and/or serum phospholipid blood levels. These conditions are oftentimes associated with a number of blood circulatory related diseases among which the most serious is arthereosclerosis.

The process for controlling hyperlipidemia of the instant invention comprises treating a mammal subject to one or more of these conditions with a hyperlipidemia controlling effective amount of a compound having the structural formula

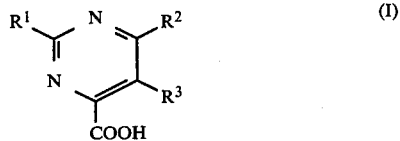

where $R^1$ is mercapto, amino, hydroxy or $C_1$–$C_4$ alkylthio; $R^2$ is amino, hydroxy or mercapto; and $R^3$ is hydrogen, $C_1$–$C_6$ alkyl, $C_7$–$C_9$ alkoxyphenyl or $C_7$–$C_9$ aralkyl.

More preferably, the process of the present invention involves controlling hyperlipidemia in mammals by treating a mammal with a hyperlipidemia controlling effective amount of a compound having Structural Formula (I) where $R^1$ is mercapto, amino, hydroxy or $C_1$–$C_2$ alkylthio; $R^2$ is amino, hydroxy or mercapto; and $R^3$ is hydrogen or $C_1$–$C_4$ alkyl.

Still more preferably, the process of the instant invention is directed to controlling hyperlipidemia in mammals by treating mammals suffering from hyperlipidemia with a hyperlipidemia controlling effective amount of a compound having Structural Formula (I) where $R^1$ is mercapto or amino; $R^2$ is amino or hydroxy; and $R^3$ is $C_1$–$C_3$ alkyl.

Of the compounds within the contemplation of the generic class, defined by Structural Formula (I), the following non-limiting group of compounds are preferred for use in the present invention: 2-mercapto-5-methyl-6-aminopyrimidine4-carboxylic acid; 2-ethylthio-5-ethyl-6-hydroxypyrimidine-4-carboxylic acid; 2-amino-5-propyl-6-aminopyrimidine-4-carboxylic acid; 2-amino-6-hydroxypyrimidine-4-carboxylic acid; 2-hydroxy-5-methyl-6-mercaptopyrimidine-4-carboxylic acid; 2-hydroxy-6-hydroxypyrimidine-4-carboxylic acid; 2-mercapto-5-methyl-6-hydroxypyrimidine-4-carboxylic acid; 2-hydroxy-5-isobutyl-6-aminopyrimidine-4-carboxylic acid; 2-amino-5-methyl-6-hydroxypyrimidine-4-carboxylic acid; 2-hydroxy-5-methyl-6-mercaptopyrimidine-4-carboxylic acid; 2-amino-5-methyl-6-mercaptopyrimidine-4-carboxylic acid; 2-amino-5-ethyl-6-aminopyrimidine-4-carboxylic acid; 2-amino-5-n-butyl-6-aminopyrimidine-4-carboxylic acid; 2-amino-5-isobutyl-6-aminopyrimidine-4-carboxylic acid; 2-amino-5-benzyl-6-aminopyrimidine-4-carboxylic acid; 2-amino-5-p-methoxyphenyl-6-aminopyrimidine-4-carboxylic acid; 2-hydroxy-5-p-methoxyphenyl-6-aminopyrimidine-4-carboxylic acid; 2-mercapto-5-ethyl-6-aminopyrimidine-4-carboxylic acid; 2-mercapto-5-n-propyl-6-aminopyrimidine4-carboxylic acid; 2-mercapto-5-n-butyl-6-aminopyrimidine-4carboxylic acid; 2-mercapto-5-benzyl-6-aminopyrimidine-4-carboxylic acid; and 2-mercapto-5-p-methoxyphenyl-6-amino- pyrimidine-4-carboxylic acid.

Consistant with the preferred and more preferred embodiments of the present invention 2-mercapto-5-methyl-6- aminopyrimidine-4-carboxylic acid; 2-ethylthio-5-ethyl-6- hydroxypyrimidine-4-carboxylic acid; 2-hydroxy-5-isobutyl-6- aminopyrimidine-4-carboxylic acid; 2-amino-5-n-propyl-6- aminopyrimidine-4-carboxylic acid; and 2-mercapto-5-methyl-6- hydroxypyrimidine-4-carboxylic acid are species particularly preferred in the process of the present invention.

In a preferred embodiment of the process of the present invention a hyperlipidemia controlling effective amount of a compound within the contemplation of the present invention is provided by treating a mammal with a compound within the contemplation of Structural Formula (I) with a concentration of between about 10 to 60 milligrams per kilogram of mammalian body weight per day. More preferably, a compound within the contemplation of the present invention is utilized in the process of the instant invention at a rate in the range of between about 12 and 40 milligrams per kilogram of mammalian body weight per day. Most preferably, the hyperlipidemia controlling effective amount of a compound within the contemplation of the present invention is in the range of between about 15 and 30 milligrams per kilogram of mammalian body weight per day.

In another aspect of the present invention a pharmaceutical composition is provided. The composition of the present invention comprises a compound defined by Structural Formula (I) where $R^1$ is mercapto, amino, hydroxy or $C_1$–$C_4$ alkylthio; $R^2$ is amino, hydroxy or mercapto; and $R^3$ is hydrogen, $C_1$–$C_6$ alkyl, $C_7$–$C_9$ alkoxyphenyl or $C_7$–$C_9$ aralkyl and a pharmaceutically acceptable carrier therefor.

More preferably, the composition of the present invention comprises a compound within the meaning of Structural Formula (I) where $R^1$ is mercapto, amino, hydroxy or $C_1$–$C_2$ alkylthio; $R^2$ is amino, hydroxy or mercapto; and $R^3$ is hydrogen or $C_1$–$C_4$ alkyl and a pharmaceutically acceptable carrier therefor.

Most preferably the composition of the present invention comprises a compound having a structural formula defined by Compound (I) wherein $R^1$ is mercapto or amino; $R^2$ is amino or hydroxy; and $R^3$ is $C_1$–$C_3$ alkyl and a pharmaceutical carrier therefor.

Pharmaceutically acceptable carriers within the contemplation of the current invention include solvents, dispersion media, coatings, antibacterial and antifungal agents, isotonic and absorption delaying agents and the like. The use of such media and agents for pharmaceutically active substances is known in the art. Except insofar as any conventional medium or agent is incompatible with the active ingredient of the present invention, its use in the hypolipidemic compositions of this invention is contemplated. Supplementary active ingredients can also be incorporated into the composition of the instant invention.

The compositions of the present invention may be prepared for oral or parenteral administration. When administration parenterally, that is, subcutaneously intraperitoneally, intramuscularly or intravenously, the carrier may be water, buffered saline, ethanol, polyol, i.e., glycerol, propylene glycol and liquid polyethylene glycol, mixtures thereof, vegetable oils and the like. To prevent microorganism contamination, the carrier of the composition of the present invention may include antibacterial and/or antifungal agents such as parabens, chlorobutanol, phenol, sorbic acid, thimerosal and the like. In addition, isotonic agents, for example, glucose or sodium chloride, may also be included in the pharmaceutically acceptable carrier of the composition of the present invention.

In the case of parenterally administered hypolipidemic compositions it is especially advantageous to formulate the composition in dosage units. Such formulation provides a uniform dosage thus improving active agent administration. Dosage unit means the physically discrete unit suited for unitary administration. That is, each unit contains a predetermined quantity of active material calculated to produce the desired hypolipidemic effect in association with the required pharmaceutical carrier. The actual dosage units of the composition of this invention will be dictated by and directly dependent upon the unique characteristics of the active material of the instant invention and the particular hypolipidemic effect to be achieved. It is within the skill of the physician to determine the exact dose appropriate for the subject involved.

In addition to the carriers discussed above for use in parenteral composition, additional carriers may be utilized in orally administered compositions. Carriers for orally administered pharmaceutically acceptable compositions include ingredients useful in the formation of tablets or capsules. Among the pharmaceutically acceptable carriers suitable for orally administered compositions are such excipients as starch, milk sugar, clays and the like. The tablets and capsules carrier may include an enteric coating in order to be resistant to the acid and digestive enzymes of the stomach.

Although any of the pharmaceutically acceptable carriers discussed above may be combined with the active compound of the present invention, the 4-pyrimidine carboxylic acids having Structural Formula (I), a particularly preferred carrier is carboxymethylcellulose (CMC). Specifically, a 1% aqueous solution of CMC is a preferred carrier for the composition of the present invention.

The following examples are given to illustrate the scope of the present invention. Because these examples are given for illustrative purposes only, the invention embodied herein should not be limited thereto.

EXAMPLE 1

Testing of Normal Mice with Compounds 1-19

Nineteen compounds, Compounds 1-19, as defined in Table 1 below, were suspended in an aqueous 1 percent carboxymethylcellulose (CMC) solution and homogenized. Each of the so prepared compounds was administered to a group of six $CF_1$ male mice, each weighting approximately 25 grams, intraperitoneally for 16 days. Each of these compounds was provided in a dosage of 20 mg/kg/d ip. In addition, Compounds 1 and 2 were provided in a concentration of 30 mg/kg/d ip. On Days 9 and 16 blood was obtained by tail vein bleeding. The blood serum so obtained was separated by centrifugation for three minutes. Serum cholesterol levels were determined by a modification of the Liebermann-Burchard reaction (Ness, *Clin. Chim. Acta.*, Vol. 10, 229 [1964]). Serum triglyceride levels were determined on Day 16 by use of the Fisher, Hycel Triglyceride Test Kit.

In addition to the above-described treated mice, an untreated control group of six mice were similarly tested on Days 9 and 16 to determine their serum cholesterol and triglyceride blood levels. Based on the results obtained for the untreated control group, the percent control, based on serum cholesterol and serum triglyceride levels of the treated mice compared to the untreated mice, was obtained. Table 2 reports this percent control, including standard deviation, indicating the level of confidence of these numbers.

COMPARATIVE EXAMPLE 1

Testing of Normal Mice with Orotic Acid

Example 1 was repeated with the exception that the test compound, Compound C1, was orotic acid (2,6-dihydroxy-pyrimidine-4-carboxylic acid), identified structurally in Table 1. The results of testing a group of six $CF_1$ male mice (each about 25 g) with this compound at concentrations of 20 and 30 mg/kg/d ip are included in Table 2.

COMPARATIVE EXAMPLE 2

Testing of Normal Mice with CMC

Example 1 was repeated except that the material injected into a group of six $CF_1$ male mice (~25 g) intraperitonerally was 1 percent CMC. The results of this test are also summarized in Table 2.

TABLE 1

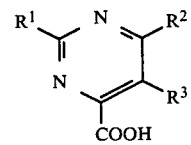

| Comp'd No. | $R^1$ | $R^2$ | $R^3$ |
|---|---|---|---|
| 1 | $NH_2$ | OH | $CH_3$ |
| 2 | SH | OH | $CH_3$ |
| 3 | OH | SH | $CH_3$ |
| 4 | SH | $NH_2$ | $CH_3$ |
| 5 | $NH_2$ | SH | $CH_3$ |
| 6 | $NH_2$ | $NH_2$ | $C_2H_5$ |
| 7 | $NH_2$ | $NH_2$ | $n-C_3H_7$ |
| 8 | $NH_2$ | $NH_2$ | $n-C_4H_9$ |
| 9 | $NH_2$ | $NH_2$ | $iso-C_4H_9$ |
| 10 | $NH_2$ | $NH_2$ | $CH_2C_6H_5$ |
| 11 | $NH_2$ | $NH_2$ | $p-C_6H_4OCH_3$ |
| 12 | OH | $NH_2$ | $iso-C_4H_9$ |
| 13 | OH | $NH_2$ | $p-C_6H_4OCH_3$ |
| 14 | SH | $NH_2$ | $C_2H_5$ |
| 15 | SH | $NH_2$ | $n-C_3H_7$ |
| 16 | SH | $NH_2$ | $n-C_4H_9$ |
| 17 | SH | $NH_2$ | $CH_2C_6H_5$ |
| 18 | SH | $NH_2$ | $p-C_6H_4OCH_3$ |
| 19 | $SC_2H_5$ | OH | $C_2H_5$ |
| 20 | $NH_2$ | OH | H |
| 21 | OH | SH | $CH_3$ |
| 22 | OH | OH | H |

TABLE 2

| Comp'd No. | Dosage, mg/kg/d ip | Serum Cholesterol Level* Day 9 | Serum Cholesterol Level* Day 16 | Serum Triglyceride Level* Day 16 |
|---|---|---|---|---|
| C1 | 20 | 91 ± 5 | 68 ± 3 | 82 ± 6 |
|  | 30 | 94 ± 4 | 76 ± 4 | 65 ± 5 |
| 1 | 20 | 84 ± 4 | 82 ± 4 | 76 ± 6 |
|  | 30 | 78 ± 3 | 77 ± 3 | 56 ± 6 |
| 2 | 20 | 80 ± 5 | 75 ± 5 | 74 ± 6 |
|  | 30 | 61 ± 4 | 66 ± 3 | 58 ± 5 |
| 3 | 20 | 75 ± 5 | 65 ± 3 | 68 ± 5 |
| 4 | 20 | 76 ± 5 | 56 ± 3 | 48 ± 4 |
| 5 | 20 | 69 ± 5 | 66 ± 4 | 59 ± 6 |
| 6 | 20 | 95 ± 5 | 73 ± 5 | 71 ± 5 |
| 7 | 20 | 101 ± 5 | 60 ± 4 | 57 ± 5 |
| 8 | 20 | 73 ± 4 | 78 ± 3 | 89 ± 7 |
| 9 | 20 | 103 ± 5 | 74 ± 4 | 53 ± 6 |
| 10 | 20 | 99 ± 6 | 73 ± 3 | 68 ± 6 |
| 11 | 20 | 68 ± 4 | 71 ± 4 | 81 ± 7 |
| 12 | 20 | 81 ± 3 | 56 ± 5 | 43 ± 4 |
| 13 | 20 | 81 ± 3 | 73 ± 4 | 73 ± 5 |
| 14 | 20 | 79 ± 6 | 68 ± 5 | 63 ± 3 |

TABLE 2-continued

| Comp'd No. | Dosage, mg/kg/d ip | Serum Cholesterol Level* | | Serum Triglyceride Level* |
|---|---|---|---|---|
| | | Day 9 | Day 16 | Day 16 |
| 15 | 20 | 78 ± 5 | 71 ± 5 | 94 ± 6 |
| 16 | 20 | 97 ± 7 | 68 ± 3 | 74 ± 7 |
| 17 | 20 | 82 ± 8 | 69 ± 4 | 50 ± 4 |
| 18 | 20 | 80 ± 5 | 64 ± 3 | 80 ± 5 |
| 19 | 20 | 70 ± 6 | 56 ± 3 | 64 ± 3 |
| CMC | — | 100 ± 6 | 100 ± 5 | 100 ± 7 |

*Reported as percentage of serum cholesterol or serum triglyceride level in control plus or minus the standard deviation.

EXAMPLE 2

Additional Testing of Normal Mice with Compounds 2, 4, 7, 12, 19 and 20–22

Example 1 was repeated, employing five of the compounds tested in Example 1, Compounds 2, 4, 7, 12 and 19 as well as three additional compounds, Compounds 20–22, defined in Table 1. All of the eight compounds tested in this example were tested on groups of six CF, male mice at a dosage of 20 mg/kg/d ip. In addition, Compound 4 was also tested at 5, 20 and 40 mg/kg/d ip.

The results of this example are summarized in Table 3.

COMPARATIVE EXAMPLE 3

Testing of Normal Mice with CMC

Example 2 was repeated except that the group of six male $CF_1$ mice were treated with a 1 percent aqueous solution of carboxymethylcellulose. The results of this comparative run are included in Table 3.

TABLE 3

| Comp'd No. | Dosage, mg/kg/d ip | Serum Cholesterol Level* | | Serum Triglyceride Level* |
|---|---|---|---|---|
| | | Day 9 | Day 16 | Day 16 |
| Control 1% CMC | — | 100 ± 7 | 100 ± 6 | 100 ± 7 |
| 2 | 20 | 84 ± 7 | 79 ± 6 | 55 ± 3 |
| 4 | 5 | 92 ± 8 | 52 ± 4 | 52 ± 5 |
| 4 | 10 | 74 ± 6 | 50 ± 5 | 53 ± 6 |
| 4 | 20 | 67 ± 8 | 45 ± 4 | 46 ± 7 |
| 4 | 40 | 77 ± 7 | 52 ± 5 | 48 ± 6 |
| 7 | 20 | 101 ± 8 | 60 ± 5 | 57 ± 7 |
| 12 | 20 | 91 ± 7 | 65 ± 6 | 43 ± 4 |
| 19 | 20 | 70 ± 8 | 56 ± 6 | 64 ± 6 |
| 20 | 20 | 81 ± 8 | 73 ± 7 | 73 ± 7 |
| 21 | 20 | 74 ± 7 | 65 ± 6 | 68 ± 6 |
| 22 | 20 | 94 ± 8 | 76 ± 6 | 65 ± 4 |

*Level reported as a percentage of the serum concentration in the control plus or minus standard deviation.

EXAMPLE 3 AND COMPARATIVE EXAMPLE 4

Serum Testing of Normal Rats

A test solution of Compound 4, 2-mercapto-6-amino-5-methylpyrimidine-4-carboxylic-acid, was suspended in an aqueous solution of 1% CMC, homogenized and administered orally to six Sprague-Dawley male rats, which each weighed approximately 350 grams. Administration of Compound 4 was by an intubation needle. The rats were each fed with 20 milligrams of Compound 4 per kilogram of body weight per day for 14 days. Similarly, six Sprague-Dawley male rats of approximately the same weight were fed similar volumes of the same aqueous 1% CMC solution without the active agent, Compound 4, also orally, administered by intubation needle. In addition, as a control, a similar group of six male Sprague-Dawley rats were untreated.

On Days 9 and 14, blood was obtained from each of the rats of the three groups by tail vein bleeding. The blood obtained was separated by centrifugation for three minutes. Serum cholesterol and triglyceride levels were determined in accordance with the procedure of Example 1.

The results of this test indicated that the serum cholesterol level of the rats treated with the inert agent, the 1 percent CMC solution, was 100 percent plus or minus 8 percent on Day 9 and 100 percent plus or minus 7 percent on Day 14 compared to the serum cholesterol level of the control rats. However, the rats treated with Compound 4 of the present invention were found to have a serum cholesterol level 71 percent plus or minus 7 percent and on Day 14, 67 percent plus or minus 8 percent compared to the average serum cholesterol level of the control rats.

The serum triglyceride test demonstrated a serum triglyceride concentration of 100 percent plus or minus 7 percent for the group of rats treated with the aqueous 1 percent CMC solution on Day 9 and a serum triglyceride level of 100 percent plus or minus 9 percent on Day 14 compared to the average serum triglyceride concentration of the control rats.

The rats treated with a concentration of 20 mg/kg/d of Compound 4 of the present invention had an average serum triglyceride level of 49 percent plus or minus 7 percent on Day 9 and a serum triglyceride level of 47 percent plus or minus 6 percent on Day 14 compared to the serum triglyceride average level of the control mice.

EXAMPLE 4

Testing of Hyperlipidemic Mice

A group of six $CF_1$ male mice (about 25 g) were placed on a commercial diet (U.S. Biochemical Corporation Basal Atherogenic Test Diet) which produced a "hyperlipidemic" state. That is, the average serum cholesterol level in the group of treated mice was raised from 125 to 354 mg percent and triglyceride levels were raised from 137 to 367 mg/dL.

Upon reaching these hyperlipidemic levels, the mice were administered Compound 4 in a concentration of 20 mg/kg/d intraperitoneally for 14 days. On Day 12, serum cholesterol and serum triglyceride levels were measured in accordance with the procedure of Example 1. The serum cholesterol level was found to be lowered from 354 mg % to 269 mg % while the serum triglyceride level was reduced from 367 mg/dL to 192 mdL.

EXAMPLE 5 AND COMPARATIVE EXAMPLE 5

Serum Lipoprotein Fraction Testing of Male Rats

A group of six Sprague-Dawley male rats (about 350 g) were orally treated with 20 mg/kg/d of 2-mercapto-6- amino-5-methyl-4-carboxylic acid (Compound 4) for 14 days. A similar group of six Sprague-Dawley male rats (about 350 g) were treated with an inert 1 percent aqueous solution of CMC. Blood from the abdominal vein and lipoprotein fractions were obtained from both sets of rats by the method of Hatch and Lee (*Adv. Lipid Res.* 1968, 6, 1) and Havel et al. (*J. Clin. Invest.* 1955, 34, 1345). Each of the fractions was analyzed for serum cholesterol, triglyceride, neutral lipid, phospholipid and protein levels.

The results of this test are summarized in Table 4.

TABLE 4

| | PERCENT OF CONTROL | | | | |
|---|---|---|---|---|---|
| | Lipids, mg | Cholesterol | Triglyceride | Phospholipid | Protein |
| Liver | | | | | |
| Control | 100 ± 6 | 100 ± 7[b] | 100 ± 5[c] | 100 ± 9[d] | 100 ± 6[e] |
| Treated | 103 ± 7 | 103 ± 7 | 110 ± 8 | 70 ± 8 | 109 ± 7 |
| Small Intestine | | | | | |
| Control | 100 ± 5 | 100 ± 7[f] | 100 ± 5[g] | 100 ± 8[h] | 100 ± 7[i] |
| Treated | 107 ± 7 | 80 ± 6* | 124 ± 7* | 119 ± 8 | 93 ± 9 |
| Feces | | | | | |
| Control | 100 ± 7 | 100 ± 8[j] | 100 ± 6[k] | 100 ± 9[l] | 100 ± 8[m] |
| Treated | 103 ± 9 | 103 ± 11 | 97 ± 8 | 96 ± 8 | 90 ± 9 |
| Chylomicrons | | | | | |
| Control | — | 100 ± 9[n] | 100 ± 8[o] | 100 ± 8[p] | 100 ± 7[q] |
| Treated | — | 79 ± 8 | 86 ± 6 | 94 ± 7 | 81 ± 9 |
| VLDL[r] | | | | | |
| Control | — | 100 ± 8[s] | 100 ± 9[t] | 100 ± 8[u] | 100 ± 8[v] |
| Treated | — | 76 ± 5* | 30 ± 2* | 102 ± 7 | 96 ± 6 |
| LDL[w] | | | | | |
| Control | — | 100 ± 9[x] | 100 ± 7[y] | 100 ± 7[z] | 100 ± 8[aa] |
| Treated | — | 46 ± 4* | 99 ± 8* | 100 ± 8 | 98 ± 9 |
| HDL[bb] | | | | | |
| Control | — | 100 ± 8[cc] | 100 ± 9[dd] | 100 ± 6[ee] | 100 ± 8[ff] |
| Treated | — | 153 ± 7* | 102 ± 8 | 108 ± 8 | 105 ± 9 |

FOOTNOTES
[a] n = 6; *p 0.001; all values expressed as X ± SD.
[b] 24.03 mg of cholesterol per gram of tissue.
[c] 6.37 mg of triglyceride per gram of tissue.
[d] 7.19 mg of phospholipid per gram of tissue.
[e] 4.5 mg of protein per gram of tissue.
[f] 7.82 mg/g.
[g] 1.12 mg/g.
[h] 2.06 mg/g.
[i] 42 mg/g.
[j] 28.47 mg/g.
[k] 1.86 mg/g.
[l] 1.39 mg/g.
[m] 6.99 mg/g.
[n] 337 ug/mL.
[o] 420 ug/mL.
[p] 149 ug/mL.
[q] 184 ug/mL.
[r] VLDL = very-low-density lipoprotein.
[s] 190 ug/mL.
[t] 22 ug/mL.
[u] 26 ug/mL.
[v] 50 ug/mL.
[w] LDL = low-density lipoprotein.
[x] 210 ug/mL.
[y] 45 ug/mL.
[z] 41 ug/mL.
[aa] 122 ug/mL.
[bb] HDL = high-density lipoprotein.
[cc] 544 ug/mL.
[dd] 27 ug/mL.
[ee] 153 ug/mL.
[ff] 657 ug/mL.

A review of Table 4 demonstrates the beneficial effects of utilization of 2-mercapto-6-amino-5-methyl-pyrimidine-4-carboxylic acid, a compound within the contemplation of the class of compounds within the process and composition of the present invention, on rat serum lipoprotein fractions. Among these effects is the significant increase (53%) in the cholesterol content of the HDL (high-density lipoprotein) fraction. High cholesterol content in this fraction in humans is generally believed to protect against cardiovascular accidents.

A second major showing depicted in Table 4 is the marked reduction in cholesterol content of the LDL (low-density lipoprotein) fraction. The LDL carries cholesterol to the tissue and arthereogenic plaques. Thus, lowering the cholesterol content showed lower deposition of cholesterol in the vessel plaques.

A third major finding of Table 4 is that the VLDL (very-low-density lipoprotein) fraction, which is usually high in triglyceride and neutral lipid content and which carries these lipids from the liver to the tissues, was markedly reduced after treatment with Compound 4.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the instant invention should be limited only by the appended claims.

What is claimed is:

1. A process for treating hyperlipidemia in mammals comprising treating a mamma in need thereof with a hyperlipidemia controlling effective amount with a compound having the structural formula

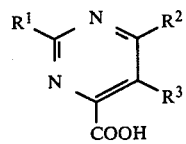

where $R^1$ is mercapto, amino, hydroxy or $C_1$-$C_4$ alkylthio; $R^2$ is amino, hydroxy or mercapto; and $R^3$ is hydrogen, $C_1$-$C_6$ alkyl, $C_7$-$C_9$ alkoxyphenyl or $C_7$-$C_9$ aralkyl.

2. A process in accordance with claim 1 wherein $R^1$ is mercapto, amino, hydroxy or $C_1$-$C_2$ alkylthio; and $R^2$ is amino, hydroxy or mercapto; and $R^3$ is hydrogen or $C_1$-$C_4$ alkyl.

3. A process in accordance with claim 2 wherein $R^1$ is mercapto or amino; $R^2$ is amino or hydroxy; and $R^3$ is $C_1$-$C_3$ alkyl.

4. A process in accordance with claim 3 wherein said compound is 2-mercapto-5-methyl-6-aminopyrimidine-4-carboxylic acid.

5. A process in accordance with claim 3 wherein said compound is 2-amino-5-n-propyl-6-aminopyrimidine-4-carboxylic acid.

6. A process in accordance with claim 3 wherein said compound is 2-mercapto-5-methyl-6-aminopyrimidine-4-carboxylic acid.

7. A process in accordance with claim 2 wherein said compound is 2-ethylthio-5-ethyl-6-hydroxypyrimidine-4-carboxylic acid.

8. A process in accordance with claim 2 wherein said compound is 2-hydroxy-5-isobutyl-6-aminopyrimidine-4-carboxylic acid.

9. A process in accordance with claim 1 wherein said hyperlipidemia controlling effective amount of said hyperlipidemia controlling compound is in the range of between about 10 and 60 milligrams per kilogram of mammalian body weight per day.

10. A process in accordance with claim 9 wherein said hyperlipidemia controlling effective amount of said hyperlipidemia controlling compound is in the range of between about 12 and 40 milligrams per kilogram of mammalian body weight per day.

11. A process in accordance with claim 10 wherein said hyperlipidemia controlling effective amount of said hyperlipidemia controlling compound is in the range of between about 15 and 30 milligrams per kilogram of mammalian body weight per day.

* * * * *

UNITED STATES PATENT AND TRADEMARK OFFICE
CERTIFICATE OF CORRECTION

PATENT NO. : 4,689,328

DATED : August 25, 1987

INVENTOR(S) : Iris H. Hall, et al.

It is certified that error appears in the above-identified patent and that said Letters Patent is hereby corrected as shown below:

Column 10, line 18, Claim 1: "mamma" should read as

--mammal--

Signed and Sealed this

Nineteenth Day of January, 1988

Attest:

DONALD J. QUIGG

Attesting Officer

Commissioner of Patents and Trademarks